| United States Patent [19] | [11] | 4,410,623 |
|---|---|---|
| DoMinh et al. | [45] | Oct. 18, 1983 |

[54] PHTHALALDEHYDE ADDUCT AND IMAGING COMPOSITIONS, ELEMENTS AND METHODS INCORPORATING SAME

[75] Inventors: Thap DoMinh; Max H. Stern, both of Rochester, N.Y.

[73] Assignee: Eastman Kodak Company, Rochester, N.Y.

[21] Appl. No.: 273,544

[22] Filed: Jun. 15, 1981

[51] Int. Cl.³ .............................................. G03C 1/52
[52] U.S. Cl. .................................. 430/341; 430/340; 430/336; 430/936; 430/178; 430/179; 430/338

[58] Field of Search ............... 430/336, 338, 340, 936, 430/341, 178, 179

[56] References Cited

U.S. PATENT DOCUMENTS 4,273,860  6/1981  Adin .................................... 430/936

Primary Examiner—Won H. Louie, Jr.
Attorney, Agent, or Firm—Dana M. Schmidt

[57] ABSTRACT

Novel adducts of phthalaldehyde are disclosed, as well as imaging compositions and imaging elements incorporating them. A method is also disclosed for minimizing dimensional changes in the element during processing.

13 Claims, No Drawings

PHTHALALDEHYDE ADDUCT AND IMAGING COMPOSITIONS, ELEMENTS AND METHODS INCORPORATING SAME

FIELD OF THE INVENTION

This invention relates to a non-silver imaging element containing energy-activatible materials that generate amines, and a method of minimizing thermal distortion of such elements.

BACKGROUND OF THE INVENTION

Extensive developments have occurred in imaging elements based upon non-silver, energy-activatible materials that generate amines to react to form a dye. Examples of such elements are set forth in *Research Disclosure*, Vol. 184, Pub. No. 18436, Aug., 1979, published by Industrial Opportunities Ltd, Homewell, Havant, Hampshire, United Kingdom. Particularly preferred are those in which o-phthalaldehyde, hereinafter phthalaldehyde, is included in the imaging composition to react with the imagewise-released amines to form the dye.

Although such imaging elements have proven to be highly successful, there have been aspects of these elements for which improvement has been sought. A particular problem has been the volatility of the phthalaldehyde. Such volatility has required some selectivity in the binder used with the composition. U.S. Pat. No. 4,247,625, issued on Jan. 27, 1981, describes a polysulfonamide binder that has proven unexpectedly superior retention of the volatile phthalaldehyde. Overcoats that aid further in retaining the phthalaldehyde have also been described. Nevertheless, such specialized binders and overcoats have added to the cost of the element.

Yet another aspect of these imaging elements has been the dimensional changes that occur when the element is heated to cause dye development, for example, at temperatures exceeding 100° C. Some of these changes can be shown to be image dependent—that is, that greater changes occur in the areas of $D_{max}$ than in the areas of $D_{min}$. Such dimensional changes are troublesome if multiple image registration is desirable, such as in the use of separation negatives or positives to create a composite image.

What has been desired, then, prior to this invention, is an imaging element that relies upon the reaction of phthalaldehyde with an amine to form dye, without using the volatile form of phthalaldehyde and without creating $D_{max}$ areas having a dimensional response to thermal processing that is different from that of the $D_{min}$ areas.

There have been disclosed in the literature certain adducts of phthalaldehyde that are not as volatile as phthalaldehyde itself. *J. Org. Chem.*, Vols. 30, 35 and 43, p. 2251 et seq, p. 3940 et seq and p. 3838 et seq.; (1965), (1970) and (1978), respectively, disclose, among others, 1-hydroxy-3-benzamidophthalan, 1-hydroxy-3-(4-chlorobenzamido)phthalan, and N-acetyl-1,3-dihydroxyisoindoline. However, these adducts are described as releasing phthalaldehyde only at very high temperatures, or as having a very complex decomposition reaction. Therefore, prior to this invention, there was reason to believe such adducts could not be relied upon to release the phthalaldehyde necessary to combine with an amine to form a dye at lower temperatures, e.g., 135° C. Furthermore, it has been discovered that, although some of these prior art compounds can in fact act as a source of phthalaldehyde, these prior art compounds produce a maximum neutral density that is less than the amount needed for preferred uses.

SUMMARY OF THE INVENTION

In accordance with one aspect of the invention, there is advantageously featured a relatively nonvolatile cyclic or open-chain adduct of phthalaldehyde that forms a dense dye when heated in the presence of an amine.

It is a related advantageous feature of the invention that such adducts can be made to release a plasticizer in proportion to the amount of dye formed.

Still another advantageous feature of the invention is that such adducts can be produced ex situ, or in situ in an imaging composition.

More specifically, there is provided an adduct of phthalaldehyde that produces a dye having a maximum neutral density of at least 1.0 when (a) an admixture is formed comprising an amount of about 3.0 mmoles of the adduct and about 0.50 mmoles of a source of amines, and (b) said admixture is coated onto a support at a rate of about 0.16 mmoles/dm$^2$ of the adduct, dried, and heated for 10 sec at a temperature of 135° C.

In accordance with another aspect of the invention, there is advantageously featured an imaging composition that relies upon a source of phthalaldehyde to produce a dye when heated in the presence of amines, the composition being improved in that the phthalaldehyde source is relatively non-volatile.

It is a related feature of the invention that such a composition is useful with binders that are not necessarily effective in retaining volatile o-phthalaldehyde, especially during heating.

It is another related feature of the invention that such a composition can be imagewise plasticized to minimize heat-induced dimensional changes that vary significantly from $D_{max}$ areas to $D_{min}$ areas.

Still another advantageous feature of the invention is that such compositions have a processing temperature for dye development that is reduced compared to such temperatures when using phthalaldehyde alone, in place of the adduct.

More specifically, there is provided an improved imaging composition comprising a source of phthalaldehyde and an energy-activatible material capable of generating an amine that reacts with the phthalaldehyde to form a dye. The composition is improved in that the source of phthalaldehyde comprises an adduct of phthalaldehyde that produces a dye when heated for 10 sec at a temperature of 135° C. in the presence of an amine, or that produces a plasticizer for the composition when heated to a temperature of 125° C.

An imaging element of the invention comprises the afore-mentioned composition disposed in one or more layers on a support.

Still another advantageous feature of the invention is a method of minimizing heat-induced dimensional changes that occur differentially in such an imaging element. More specifically, this method is provided for the above-noted imaging element and composition comprising an equilibrium amount of an adduct of (i) phthalaldehyde and (ii) a plasticizer for said composition. The method comprises the steps of (a) imagewise exposing the element to activating radiation, and thereafter (b) heating at least the areas of said exposed element that are to become the dyed areas. The heating proceeds at a temperature and for a time sufficient to cause, in the exposed areas, the amine ligands to be released, and the adduct to decompose into phthalaldehyde and the plasticizer. The phthalaldehyde combines with the amine ligands to form a dye so that the equilibrium of the adduct decomposition reaction is shifted, in the exposed areas, to produce an amount of the plasticizer that is proportional to the amount of phthalaldehyde that is reacted to form the dye.

Other features of the invention will become apparent upon reference to the following description of the preferred embodiments.

DESCRIPTION OF THE PREFERRED EMBODIMENTS

This invention concerns novel compounds, an imaging composition comprising such compounds, an element comprising the imaging composition, and a method of preventing thermal distortion in such an element. More specifically, we have discovered that novel adducts of phthalaldehyde have the property of reacting with amines to form, when heated for 10 sec at a test temperature of 135° C., a high density dye, that is, a dye with a maximum neutral density of at least 1.0. "Maximum neutral dye density" refers to the maximum density of the shoulder portion of the density-log exposure curve plotted for an exposure series of the imaging element through a neutral density step wedge. Such adducts are substantially non-volatile at the temperatures at which the element is formed and dried, and can be made to produce useful decomposition fragments in addition to the dye-forming moiety. These adducts are useful in an imaging composition to provide a source of phthalaldehyde that reacts with an amine resulting from activating an energy-activatible material to form a dye. The adduct can be formed ex situ, or in situ in the composition.

A useful simplified test procedure, hereinafter "simplified test", to determine whether an adduct has the desired property of forming a dye in the presence of an amine, when heated to a temperature of 135° C., is to add a solution of the adduct (Part A below) to the solution of Part B below, and imbibe the mixture onto filter paper. (The rate of adduct coverage of this test is not critical, and need not coincide with other coating rates noted herein. This simplified test does not require a density of at least 1.0 to be produced.) After drying under a hood for 30 minutes, exposing in a Canon Kal-Printer Model 480VC for 30 sec., (exposure distance of about 2.5 cm), and heating for 10 sec. on a 135° C. hot block, the paper is examined for a dye image.

| Part A | |
|---|---|
| adduct | 0.02 g |
| actone | 0.1 g |
| dimethylformamide | 0.05 g |
| Part B | |
| acetone | 10.0 g |
| 2-isopropoxy-1,4-naphthoquinone | 0.016 g |
| hexamminecobalt(III)trifluoroacetate | 0.24 g |

A preferred class of adducts are those having the structure

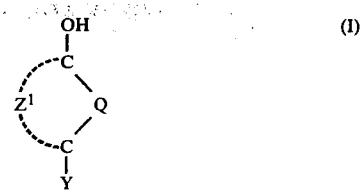

wherein
$Z^1$ is the number of atoms necessary to complete two, or three carbocyclic or heterocyclic rings of from 9 to 13 nuclear atoms;
Q is O,

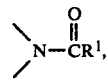

$>NSO_2R^2$, or S
Y is —OH, —OR$^5$, —CHR$^3$R$^4$,

or —NR$^6$R$^7$;
R$^1$ is

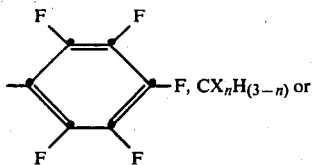 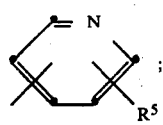

$R^2$ is alkyl or alkaryl of from 1 to 11 carbon atoms, for example, methyl, ethyl, propyl, isopropyl, p-methylphenylene, p-ethylphenylene and the like, the terms alkyl and alkaryl being understood to include those that are substituted in the alkyl portion, for example, p-(1-hydroxyethyl)phenylene;
$R^2$ further includes aryl or aralkyl of from 6 to 11 carbon atoms, for example, phenyl, naphthyl, benzyl, and the like, the term "aryl" being understood to include, in this context, substituted aryl, for example, aryl having halogen, nitro, alkyl, alkoxy, α-hydroxyalkyl, dialkylamino and/or

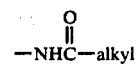

substituents. (In some examples herein, the convention followed for the substituents on the carbo- or heterocyclic rings is that hydrogen substituents are not shown since they are obvious.)
$R^3$ and $R^4$ are the same or different and are each hydrogen, —SO$_3$CH$_3$, NO$_2$, or alkyl of from 1 to 5 carbon atoms, for example, methyl, ethyl, propyl, isopropyl and the like;
$R^5$ is alkyl of from 1 to 5 carbon atoms, for example, methyl, ethyl, propyl, isopropyl and the like; or is

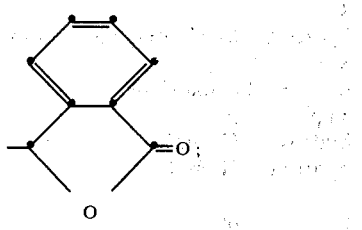

and

R[6] and R[7] are individually H or SO$_2$R[2], or together comprise the atoms necessary to complete a ring having the structure

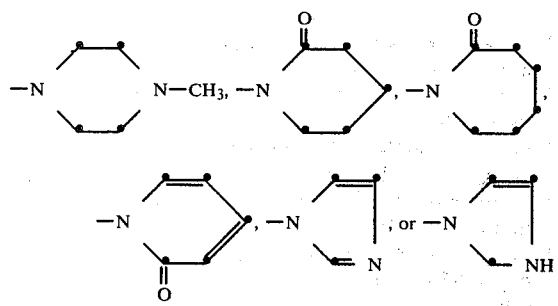

X is halogen, such as chlorine, bromine, iodine, and fluorine; and n is 1, 2, or 3.

Included in the class of adducts having the structure (I) are phthalans and isoindolines. Most preferred are phthalans having the following structural formula:

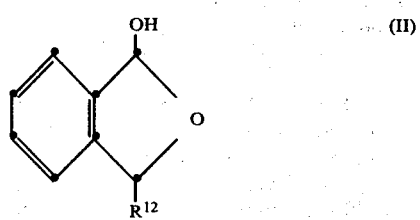

wherein

R[12] is a moiety having a structural formula selected from the group consisting of

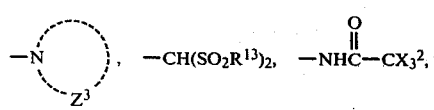

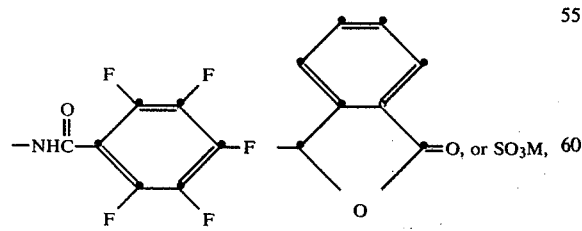

R[13] is alkyl or from 1 to 5 carbon atoms, for example, methyl, ethyl, propyl, isopropyl and the like;

X[2] is halogen, for example, chlorine, fluorine and the like;

M is a metal, such as sodium, potassium and the like; and

Z[3] represents the carbocyclic or heterocyclic atoms necessary to complete a ring having the structure

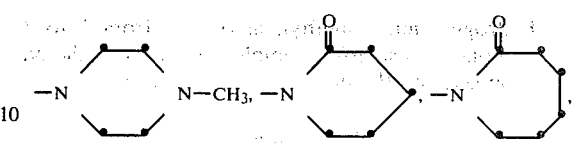

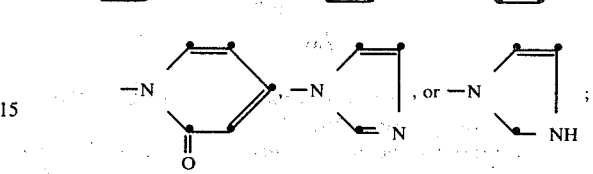

and isoindolines having the structural formula

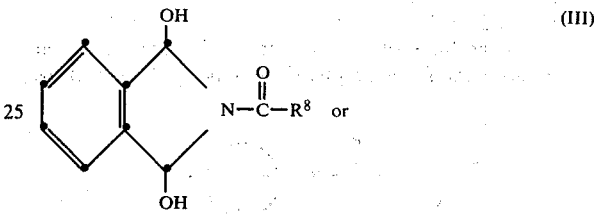

wherein

R[8] is CX$_n$H$_{(3-n)}$ or

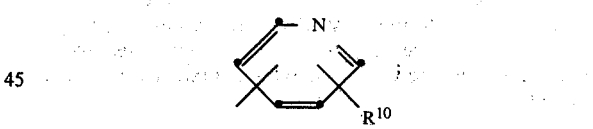

R[9] is

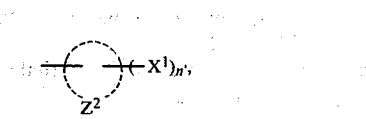

alkyl of from 1 to 3 carbon atoms, R[10] or

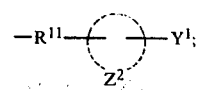

R[10] is alkyl of from 1 to 3 carbon atoms, such as methyl, ethyl, n-propyl, and isopropyl;

R[11] is —NH— or alkylene of from 1 to 5 carbon atoms, for example, methylene, ethylene, propylene, isopropylene, and the like;

X is halogen, e.g., chlorine, fluorine, and the like;

$X^1$ is halogen, e.g., chlorine, fluorine and the like;

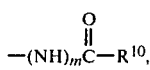

hydrogen, nitro, methyl, alkoxy of from 1 to 3 carbon atoms, for example, methoxy, ethoxy, propoxy, and the like;

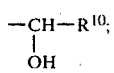

or —OM where M is a metal such as K or Na;
Y' is hydrogen or —N(R$^{10}$)$_2$;
Z$^2$ represents the atoms necessary to complete an aromatic ring of from 6 to 10 nuclear atoms, for example, phenylene and naphthalene;
m is 0 or 1;
n is 2 or 3; and
n' is 1, 2 or 3.

Useful adducts of this invention also include open-chain adducts, for example, those having the structure

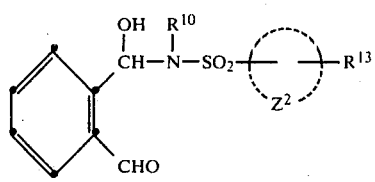

wherein R$^{10}$, R$^{13}$, and Z$^2$ are as described above. A specific compound exemplifying the structural formula (V) is N-methyl-N-(1-hydroxy-1-ortho formylphenyl)-methyl-p-toluene sulfonamide.

The following Table I is a list of the preferred adducts of the invention, along with their melting points. It will be understood that of the methods used to prepare these, discussed hereinafter, the results did not in all cases yield 100% of the named compound. In certain cases the isoindoline as well as the phthalan was produced, or vice versa. The footnotes appended to the name indicate the extent to which mixtures were produced.

TABLE I—PREFERRED ADDUCTS

Phthalans 1-hydroxy-3-(penta-fluorobenzamido)phthalan, m.p. = 111°–112° C.
1-hydroxy-3-ε-caprolactamidophthalan, m.p. = 104°–105° C.;
1-hydroxy-3-α-pyridoneamidophthalan, m.p. = 69°–70° C.;
1-hydroxy-3-δ-valerolactamidophthalan, m.p. = 88°–91° C.;
1-hydroxyphthalan-3-sulfonic acid, sodium salt, no m.p., (dec.);
1-hydroxy-3-(3'-phthalido)phthalan, m.p. not available;
1-hydroxy-3-N-imidazolinophthalan, m.p. = 126°–127° C.;
1-hydroxy-3-bis(methanesulfonyl)methanophthalan, m.p. = 206°–207° C.;
1-hydroxy-3-trichloroacetamidophthalan, m.p. = 94°–95° C.;
1-hydroxy-3-N-(N'-methylpiperazino)phthalan, m.p. = 94°–95.5° C.;

Isoindolines 1,3-dihydroxy-N-(1-naphthalenesulfonyl)isoindoline, m.p. = 108°–109° C.;
1,3-dihydroxy-N-[4-(1-hydroxyethyl)benzenesulfonyl]isoindoline, m.p. = 55°–57° C.;
1,3-dihydroxy-N-(2,5-dichloro)benzenesulfonyl]isoindoline, m.p. 124°–125° C.;
1,3-dihydroxy-N-[3-pyridinecarbonyl]isoindoline, m.p. = 128°–129° C.;
1.3-dihydroxy-N-(4-methylbenzenesulfonyl)isoindoline, m.p. = 97°–99° C.;
1,3-dihydroxy-N-(benzenesulfonyl)isoindoline, m.p. = 112°–113° C.;
1,3-dihydroxy-N-(4-acetamidobenzenesulfonyl)isoindoline, m.p. = 131°–134° C.;
1,3-dihydroxy-N-(dichloroacetyl)isoindoline,* m.p. = 121°–123° C.
1,3-dihydroxy-N-(4-chlorobenzenesulfonyl)isoindoline, m.p. = 114°–116° C.;
1,3-dihydroxy-N-(4-bromobenzensulfonyl)isoindoline m.p. = 99°–105° C.;
1,3-dihydroxy-N-(4-iodobenzenesulfonyl)isoindoline, m.p. = 127°–129°;
1,3-dihydroxy-N-(4-carbomethoxybenzenesulfonyl)isoindoline, m.p. = 98°–100° C.;
1,3-dihydroxy-N-(4-nitrobenzenesulfonyl)isoindoline 125°–126° C.;
1,3-dihydroxy-N-(methanesulfonyl)isoindoline, m.p. = 114°–116° C.;
1,3-dihydroxy-N-(α-tolylsulfonyl)isoindoline, m.p. = 123°–125° C.;

*About 60% in this form, 40% in the phthalan form.

It is contemplated that polymeric forms of the adduct are also useful. For example, a polymeric adduct is producable by either of the following reactions, in situ or ex situ;

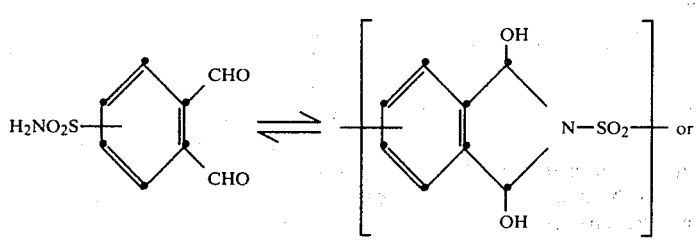

(1)

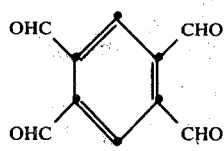 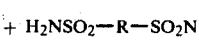 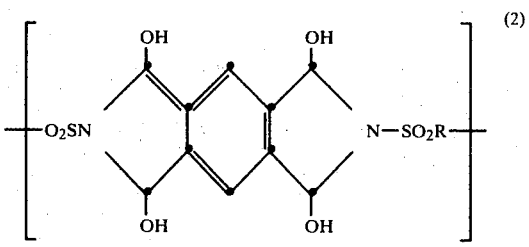

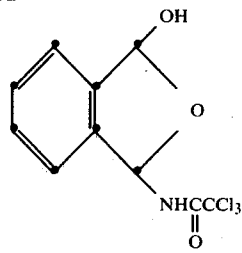

MW = 296

A significant number of the above-described adducts have a further useful property—when the adduct thermally decomposes, it releases or forms a compound that is a plasticizer for the preferred imaging composition hereinafter described. Preferred examples are the adducts that release when heated, and are formed from, sulfonamides and carbonamides. The most preferred examples of Table I having this property are 1,3-dihydroxy-N-(4-chlorobenzene sulfonyl)isoindoline; 1,3-dihydroxy-N-(4-methylbenzenesulfonyl)isoindoline; 1,3-dihydroxy-N-(4-bromobenzenesulfonyl)isoindoline; 1,3-dihydroxy-N-(4-iodobenzenesulfonyl)isoindoline; 1,3-dihydroxy-N-(4-acetamidobenzenesulfonyl)isoindoline; and 1-hydroxy-3-trichloroacetamidophthalan.

A preferred general preparation sequence for the above adducts is as follows:

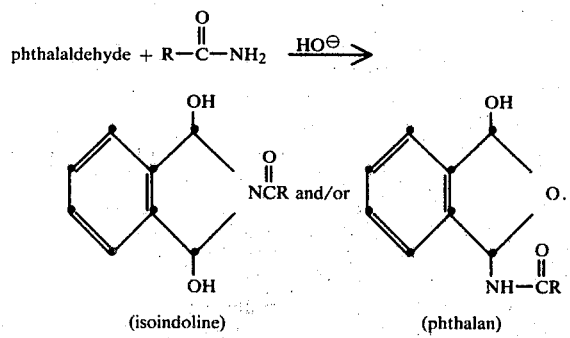

The following preparations further illustrate the manner in whch the adduct can be formed.

PREPARATION 1

Synthesis of 1-Hydroxy-3-Trichloro acetamidophthalan

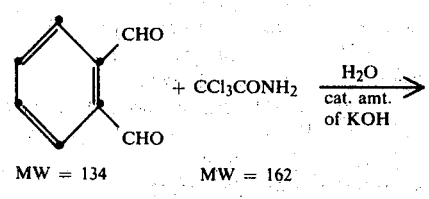

A mixture of phthalaldehyde (33.5 g, 0.25 mol) and trichloroacetamide (40.5 g, 0.25 mol) was ground to a powder with a mortar and pestle. This was suspended in water (1.5 l), stirred for 10 min and then 5 ml of 1 N KOH added. After stirring for 3 hr, the reaction mixture was allowed to settle and the supernatant layer discarded. The solid product was collected, washed three times with water and once with 20% acetonitrile in water. The solids were then dissolved in 1 l acetone at 20°–25° C., stirred for 15 min with 10 g of decolorizing charcoal and filtered through a layer of Celite adsorbent. The filtrate was diluted with water (1 l) and allowed to crystallize. The solids were collected, washed with 20% acetonitrile in water and dried in a vacuum desiccator. The solids analyzed as follows: wt 22 g (30% yield); m.p. 96°–97° C.; one spot by thin layer chromatographic analysis (TLC).

A second crop of solids [12.5 g, (17% yield) m.p. 106°–113° C.] was obtained by chilling the filtrate fractions. Both crops of products were identical by TLC and infrared analysis (no phthalaldehyde present) and showed the phthalin structure by $^{13}$C-NMR.

Anal. Calc'd for $C_{10}H_8Cl_3NO_3$: C, 40.5; H, 2.7; Cl, 35.9; N, 4.7. Found: C, 40.2; H, 2.8; Cl, 35.6, N, 5.2.

PREPARATION 2

Synthesis of 1,3-Dihydroxy-N-(4-methylbenzene sulfonyl)isoindoline

An intimately ground mixture of recrystallized phthalaldehyde (33.5 g, 0.25 mol) and p-toluenesulfonamide (44.9 g, 0.26 mol) was suspended in distilled water (1.5 l). To the vigorously stirred mixture was added 1 N KOH (5 ml, 0.005 mol) and stirring continued for 1 hr. The solids were collected and recrystallized from acetone (125 ml) and water (~300 ml) at 5°–20° C. The crystals were collected and dried under vacuum for 48 hrs producing: wt=66 g (86% yield), m.p.=97°–99° C.

Anal. Calc'd for $C_{15}H_{15}NO_4S$: C, 58.8; H, 5.0; N, 4.6; S, 10.5 Found: C, 58.8; H, 5.1; N, 5.6; S, 10.5.

$^{13}$C-NMR indicated the composition was mainly in the isoindoline form, with some phthalan. IR indicated no phthalaldehyde at ~1700 cm$^{-1}$.

PREPARATION 3

Synthesis of 1,3-Dihydroxy-N-(dichloroacetyl)isoindoline and 1-hydroxy-3-dichloroacetamidophthalan A mixture of phthalaldehyde (13.4 g, 0.1 mol) and a solution of dichloroacetamide (12.8 g, 0.1 mol) in water (200 ml) was stirred for 10 min. Then a quantity of 1 M KOH (0.01 mol) was added and stirring continued for 12 hr. Adduct formation was complete as noted by the absence of phthalaldehyde on TLC analysis of an aliquot sample. The solids were collected and dried overnight in a vacuum desiccator: wt 19.8 g (75.8% yield). Recrystallization, at 5° C., of a 5 g sample from acetonitrile (5 ml) and a little pentane gave 4.3 g of a light yellow solid, m.p. 122°-123° C. This product was characterized by $^{13}$C-NMR as an approximate 60:40 mixture of

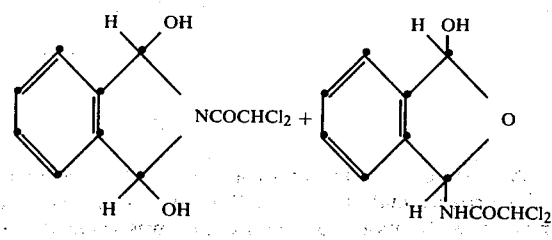

Anal. Calc'd for $C_{10}H_9Cl_2NO_3$: C, 45.8; H, 3.5; N, 5.3; Cl, 27.1 Found: C, 46.2; H, 3.3; N, 6.5; Cl, 26.0.

PREPARATION 4

Synthesis of 1-Hydroxy-3-(4-N-methyl piperazino)phthalan

A charge of 2.68 g (0.02 mol) of phthalaldehyde in dry ether (100 ml) was cooled to 5° C. and 1-methyl piperazine (2 g, 0.02 mol) added. The stirred mix was allowed to warm to 20° C. over 3 hrs and the solid adduct collected. This product (2.25 g, m.p. 94°-95.5° C., 48% yield) was characterized by IR and $^{13}$C-NMR as the phthalan.

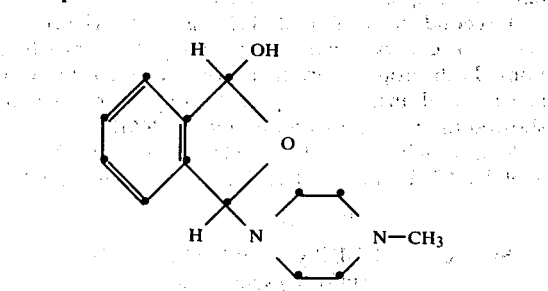

Anal. Calc'd for $C_{13}H_{18}N_2O_2$: C, 66.6; H, 7.7; N, 12.0 Found: C, 66.3; N, 7.6; N, 11.7.

It will be appreciated that the aforedescribed preparations can be achieved in situ by mixing the two starting materials within the imaging composition dope hereinafter described.

To provide the amines with which the phthalaldehyde is to react upon thermal decomposition of the adduct, any energy-activatible material that generates amines when exposed to useful energy is useful. Preferred energy-activatible materials include metallic complexes containing amine ligands that are released in response to exposure to thermal or light energy. Any such complex is useful. Highly preferred are reducible cobalt(III) complexes containing amine ligands, such as are described in Research Disclosure, Pub. 18436, Vol. 184, published August, 1979, by Homewell, Havant, Hampshire, PO9 1EF, United Kingdom. It has been found that such complexes are particularly responsive to destabilizer materials which upon exposure to the aforesaid energy cause release of the ligands. Such complexes on occasion have been described as being "inert." See, e.g., U.S. Pat. No. 3,862,842, Columns 5 and 6. However, the ability of such complexes to remain stable, i.e., retain their original ligands when stored by themselves or in a neutral solution at room temperature until a chemically or thermally initiated reduction to cobalt(II) takes place, is so well known that the term "inert" will not be applied herein.

Such cobalt(III) complexes feature a molecule having a cobalt atom or ion surrounded by a group of atoms or other molecules which are generically referred to as ligands. The cobalt atom or ion in the center of these complexes is a Lewis acid while the ligands, herein described as amine ligands, are Lewis bases. While it is known that cobalt is capable of forming complexes in both its divalent and trivalent forms, trivalent cobalt complexes—i.e., cobalt(III) complexes—are preferably employed in the practice of this invention, since the ligands are relatively tenaciously held in these complexes, and released when the cobalt is reduced to the (II) state.

Most preferably, the cobalt(III) complexes employed in the practice of this invention are those having a coordination number of 6. Many amine ligands are useful with cobalt(III) to form a useful cobalt(III) complex, including, e.g., methylamine, ethylamine, ammines, and amino acids such as glycinato. As used herein, "ammine" refers to ammonia specifically, when functioning as a ligand, whereas "amine" is used to indicate the broader class noted above. Useful complexes also include those containing other ligands in addition to the amine ligands.

The cobalt(III) complexes useful in the practice of this invention include those that are neutral compounds entirely free of either anions or cations. As used herein, "anion" refers to a charged species which, in the commonly understood sense of the term, does not include species that are covalently bonded. Useful cobalt(III) complexes also include those having one or more cations and anions as determined by the charge neutralization rule. Useful cations are those which produce readily soluble cobalt(III) complexes, such as alkali metals and quaternary ammonium cations.

Many anions are useful, and those disclosed in the aforesaid Research Disclosure are particularly useful.

The following Table II is a partial list of particularly preferred cobalt(III) complexes.

TABLE II hexa-ammine cobalt(III) benzilate
hexa-ammine cobalt(III) perfluorobenzoate
hexa-ammine cobalt(III) thiocyanate
hexa-ammine cobalt(III) trifluoromethane sulfonate
hexa-ammine cobalt(III) trifluoroacetate
hexa-ammine cobalt(III) heptafluorobutyrate
chloropenta-ammine cobalt(III) perchlorate
bromopenta-ammine cobalt(III) perchlorate
aquopenta-ammine cobalt(III) perchlorate
bis(methylamine) tetra-ammine cobalt(III) hexa-fluorophosphate trinitrotris-ammine cobalt(III)
penta-ammine carbonate cobalt(III) perchlorate
tris(glycinato) cobalt(III)
tris(trimethylenediamine) cobalt(III) trifluoromethanesulfonate
tri(trimethylenediamine) cobalt(III) tetrafluoroborate
bis(ethylenediamine)bisazido cobalt(III) perchlorate
triethylenetetraaminedichloro cobalt(III) trifluoroacetate
aquopenta(methylamine) cobalt(III) nitrate
chloropenta(ethylamine) cobalt(III) pentafluorobutanoate
trinitrotris(methylamine) cobalt(III)
tris(ethylenediamine) cobalt(III) trifluoroacetate
μ-superoxodecamine cobalt(III) perchlorate
trans-bis(ethylenediamine)chlorothiocyanato cobalt(III) perchlorate
trans-bis(ethylenediamine)bisazido cobalt(III) thiocyanate
cis-bis(ethylenediamine)ammineazido cobalt(III) trifluoroacetate
tris(ethylenediamine) cobalt(III) benzilate
trans-bis(ethylenediamine)dichloro cobalt(III) perchlorate
bis(ethylenediamine)dithiocyanato cobalt(III) perfluorobenzoate
triethylenetetraaminedinitro cobalt(III) dichloroacetate and
tris(ethylenediamine) cobalt(III) succinate.

If the activating energy used to initiate the reaction is light energy, then the energy-activatible material of this invention that generates the amines preferably includes a destabilizer that is a photoreductant responsive to that energy. Any photoreductant capable of forming a reducing agent for the amine-generating complex, in response to exposure to such activating electromagnetic energy, is useful. The development of the image initiated by such exposure preferably occurs by subsequently heating the composition to obtain a more prompt generation of the amines. A variety of useful photoreductants are disclosed, for example, in *Research Disclosure*, Vol. 126, Publication 12617, October, 1974, and U.S. Pat. No. 4,201,588 issued May 6, 1980. The details of both of these documents are expressly incorporated herein by reference. A "photoreductant" is distinguishable from other photoactivators such as spectral sensitizers in that only a photoreductant is responsive to the activating energy even in the absence of a cobalt(III) complex. Thus, the photoreductant itself is exposable, when used in a first layer without the complex. A second layer of a cobalt(III) complex thereafter placed in contact with the first layer (preferably heated) causes a reduction of the complex to take place.

Useful photoreductants include disulfides, anthrones, diazonium salts, and quinones. The quinones are particularly preferred. Preferably, a source of labile hydrogen atoms is also present either as a separately-added adjuvant such as is described in Paragraph II(C) of the last-named *Research Disclosure*, or as labile hydrogen atoms incorporated into the photoreductant in a form that increases the speed of the complex reduction, upon exposure. Incorporated hydrogen atom photoreductants are also described in the last-named *Research Disclosure*.

The quinones which are particularly useful as photoreductants include ortho- and para-benzoquinones and ortho- and para-naphthoquinones, phenanthrenequinones and anthraquinones. The quinones are unsubstituted or incorporate any substituent or combination of substituents that do not interfere with the conversion of the quinone to the corresponding reducing agent. A variety of such substituents are known in the art and include, but are not limited to, primary, secondary and tertiary alkyl, alkenyl and alkynyl, aryl, alkoxy, aryloxy, alkoxyalkyl, acyloxyalkyl, aryloxyalkyl, aroyloxyalkyl, aryloxyalkoxy, alkylcarbonyl, carboxy, primary and secondary amino, aminoalkyl, amidoalkyl, anilino, piperidino, pyrrolidino, morpholino, nitro, halide and other similar substituents. Aryl substituents are preferably phenyl substituents. Alkyl, alkenyl and alkynyl substituents, whether present as sole substituents or present in combination with other atoms, preferably contain about 20 or fewer (preferably 6 or fewer) carbon atoms.

The most preferred photoreductants presently are the internal hydrogen source quinones; that is, quinones incorporating labile hydrogen atoms as described above. These quinones are more easily photoreduced than quinones which do not incorporate labile hydrogen atoms.

Further details and a list of various quinone photoreductants of the type described above are set forth in the aforesaid *Research Disclosure*, Volume 126, October, 1974, Publication No. 12617. Still others which are useful include 2-isopropoxy-3-chloro-1,4-naphthoquinone and 2-isopropoxy-1,4-anthraquinone.

Activating electromagnetic energy of wavelengths less than 300 nm, e.g., X-rays, is also useful as an exposure mode. In such a case, a photoreductant is not a necessary part of the amine-generating material and can be omitted.

If the activating energy used to initiate the reaction is thermal in nature, thermal destabilizers of the type described in the aforesaid *Research Disclosure*, Publication No. 18436, are useful.

Still other forms of activating energy are useful, such as energetic particle radiation, for example, electron-beam radiation.

The imaging composition is either absorbed into a paper or similar fibrous material, or it is applied as a layer or layers on a support. In the latter case, a binder is preferably included in said imaging composition. Any binder compatible with cobalt(III) complexes is useful, for example, the binders listed in the aforesaid Publication No. 12617 of *Research Disclosure*, especially paragraph I(D). Typical of such binders are acetates, cellulose compounds, vinyl polymers, polyacrylates and polyesters. In addition, useful binders include certain polysulfonamides, for example, poly(ethylene-co-1,4-cyclohexylenedimethylene-1-methyl-2,4-benzenedisulfonamide), poly(ethylene-co-hexamethylene-1-methyl-2,4-benzenedisulfon-amide), and poly(methacrylonitrile).

However, according to the present invention, the polysulfonamides are not necessary to prevent the phthalaldehyde from volatilizing, as the use of the adduct eliminates such a problem. For the same reason, overcoats can be omitted.

Yet another useful binder for this invention is a homopolymer or copolymer having a recurring unit with the structure

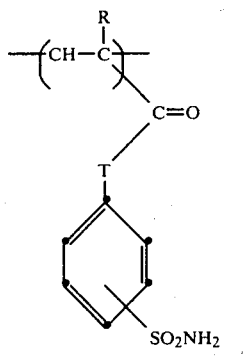

wherein T is —O— or —NH— and R is alkyl of 1 to 3 carbon atoms. The advantage of such a binder is that when phthaladehyde is imagewise released from the adduct by the heating step, the binder crosslinks by reason of the reactivity between each SO₂NH group of two different polymer chains, and the two aldehyde groups of phthalaldehyde. The resulting crosslinked polymer is less soluble than the uncrosslinked binder, permitting the developed composition to be used as a lithographic printing plate. (The support in such a case is preferably a hydrophilic support, such as a metallic plate.)

Optionally, dye formers in addition to phthalaldehyde are incorporatable in the composition, either in the same layer or a layer adjacent to the layer containing the cobalt(III) complex, provided such dye formers are responsive to either the released amines or the cobalt(II) resulting from the reduction reaction. Examples are described in the aforesaid *Research Disclosure* Publication No. 12617.

Also optionally, a photoinhibitor of the type described in the aforesaid *Research Disclosure*, Pub. No. 18436 is useful in the composition, to provide positive-working image formation in response to light exposure. The photoinhibitor is selected to be one or more compounds which themselves have a sensitivity that responds to wavelengths longer than about 300 nm, or it is selected to comprise a compound whose sensitivity responds only to wavelengths shorter than about 300 nm, and a spectral sensitizer which increases the native sensitivity to beyond 300 nm.

Any photoinhibitor having the desired property of inhibiting the release of amines in response to an exposure to activating radiation, is useful. It is preferable that the photoinhibitor be capable of being coated without extensive volatilization.

Examples and further details of the photoinhibitors are described in said *Research Disclosure*, Pub. No. 18436, the contents of which are incorporated herein by reference.

When a photoinhibitor is included, the energy-activatible material preferably is responsive to thermal energy to produce an opaque density, rather than an absence of density.

An imaging element preferably is prepared by coating or otherwise forming from solution one or more layers of the afore-described composition on a support. The simplest form of such an element comprises a support and a single layer on the support. Alternatively, the imaging composition is divided into a plurality of layers. Such plurality of layers still form an integral element, or alternatively the outermost layer is disposed subsequently in reactable association with the other layers, such as after exposure. Examples and details are described in the aforesaid *Research Disclosure* No. 18436. Useful supports are also described in the last-named *Research Disclosure*.

The coating solvent selected will, of course, depend upon the makeup of the composition, including the binder, if any. Typical preferred solvents which are used alone or in combination are lower alkanols, such as methanol, ethanol, isopropanol, t-butanol, and the like; ketones, such as methyl ethyl ketone, acetone and the like; water; ethers, such as tetrahydrofuran, and the like; acetonitrile; dimethylsulfoxide and dimethylformamide.

The proportions of the non-binder reactants forming the composition to be coated and/or the imaging element vary widely depending upon which materials are being used. Since a cobalt(III) complex preferably is present, the molar amounts are expressed per mole of complex. Thus, if destabilizer materials are incorporated in addition to cobalt(III) complex, they vary widely from about 0.004 mole per mole of complex, such as for ferrocene, to about 5 moles of other destabilizers per mole of complex. The photoinhibitor, if any, is present in an amount from between about 0.005 to about 2.5 moles per mole of cobalt(III) complex. For example, 2,4-bis(trichloromethyl)-6-(p-anisyl)-s-triazine can be present in those amounts.

A convenient range of coating coverage of cobalt(III) complex is between about 2.5 and about 25 mg/dm², and the phthalaldehyde adduct between about 10 and 50 mg/dm².

Preferably, solutions are coated onto the support by such means as whirler coating, brushing, doctor-blade coating, hopper coating and the like. Thereafter, the solvent is evaporated. Other exemplary coating procedures are set forth in the *Product Licensing Index*, Vol. 92, December, 1971, Publication No. 9232, at page 109. Addenda such as coating aids and plasticizers are useful when incorporated into the coating compositions. To provide long-term keeping or storage, it is preferred that 2,6-di-t-butyl-p-cresol be included as an antioxidant.

The afore-described imaging element is preferably imagewise exposed to activating energy, preferably light or thermal energy, and uniformly heated for 5 to 10 seconds until the cobalt(III) complex is converted to cobalt(II) and released ligands, and the adduct decomposes. The amines thus formed react with the phthalaldehyde thus formed, yielding a dye. The actual temperature of the heating step depends upon the temperature required to obtain release of the ligands from the cobalt(III) complex. That temperature is generally in the range of 125° C. to 135° C., for a heating time of 5 to 10 seconds, and in the case where the adduct releases a destabilizer fragment as described hereinafter, it can be as low as 100° C. Further details of the imaging process are set forth in *Research Disclosure* Pub. No. 20020 of Vol. 200, published December 1980, and Pub. No. 18436, Vol. 184, published August 1979, the contents of which are expressly incorporated herein by reference.

As noted above, useful phthalaldehyde adducts for the imaging element are those that imagewise release a plasticizer for the imaging composition. The need for such imagewise plasticizing is believed to arise from the fact that o-phthalaldehyde, when present as such, is itself a plasticizer. However, prior to this invention, the dye-forming mechanism resulted in consumption of the phthalaldehyde, in proportion to the density of the dye. Thus, $D_{max}$ areas have had reduced amounts of plasticizer, resulting in a different heat-induced dimensional response compared to the $D_{min}$ areas.

Although the mechanism of the imagewise plasticizing is not critical to the invention, it is believed to be as follows:

The phthalaldehyde adduct that is formed, whether ex situ or in situ, is in reality a dynamic equilibrium of the starting materials and the adduct itself in accordance with the equation $$PA\text{-}C \rightleftharpoons PA + C \qquad (i)$$

wherein PA is phthalaldehyde and C is the compound added to form the adduct. At room temperatures this reaction tends to go to the left, for the compounds C described herein. However, at elevated temperatures, for example, temperatures of 125° C., the reaction tends to go to the right. Upon cooling, the reaction reverses to the left but only in the imaging element areas that do not form dye from the phthalaldehyde. In the dye-forming areas, when the heating step is conducted at or above the initiation temperature of the reduction of the cobalt(III) complex, there occurs an extensive release of amine ligands from the cobalt complex. These ligands react with free phthalaldehyde made available from equilibrium reaction (i) above, to form the dye. This removes the phthalaldehyde from the reaction and forces the reaction to produce an amount of compound C in general proportion to the amount of phthalaldehyde removed, in accord with the well-known principles of equilibrium reactions. By selecting C to be a plasticizer for the imaging element, as described above, plasticizer is thus produced only in the element areas that require additional plasticizer because of the removal of the phthalaldehyde.

It will be appreciated that the adduct is always in equilibrium, in the coating, with some of the phthalaldehyde and the other compound forming the adduct with phthalaldehyde. That is, even if the adduct is formed ex situ and extracted from the starting material, as soon as it is added to the coating dope it will undergo decomposition to some extent, and particularly when the coating is dried by heating.

The adducts of the invention have been found to reduce the temperature required for dye development, by a mechanism that is not now completely understood. In addition, certain adducts produce a lowering of the processing temperature beyond that produced by the other adducts. It is believed that these latter adducts thermally release a fragment that acts in a manner similar to the second thermal destabilizer material described in the aforesaid *Research Disclosure,* Publication No. 20020. For example, it has been found that using 1-hydroxy-3-trichloroacetamidophthalan as the adduct, the processing temperature is reduced from 135° C. to about 100° C. A maximum neutral density in excess of 3.00 occurs for this adduct when thermal development is performed at 100° C. or 110° C. for 30 sec. Thus, adducts such as these permit thermal developments to be conducted at a temperature well below the 135° C. temperature selected to test the dye-forming capability of the adduct.

EXAMPLES

The following examples further illustrate the invention.

EXAMPLES 1–16

Imaging Elements Using Adducts Prepared Ex Situ

A coating dope was prepared according to the following Formula I (negative-working) or Formula II (positive-working) and coated at about 100-micron wet laydown on subbed poly(ethylene terephthalate) film support and dried for 10 min at 60° C. A sample of each coating was exposed at a distance of about 2.5 cm to a 0.3 log E step tablet in a Canon Kal-Printer, Model 480VC, containing three 60-watt UV-fluorescent lamps, for 30 seconds (Formula I) or 60 seconds (Formula II) and then processed by contacting the back of each sample to a heated surface set at 135° C. for 10 seconds. $D_{max}/D_{min}$ and speed were determined as listed in Table II. "$D_{max}$" is the maximum neutral density value, and "$D_{min}$" is the minimum neutral density portion of the density-log exposure curve.

| Formula I | |
|---|---|
| Poly(ethylene-co-1,4-cyclohexyl-enedimethylene-1-methyl-2,4-benzenedisulfonamide) binder (15% wt-wt in acetone) | 10.0 g |
| Hexammine cobalt(III) trifluoroacetate | 0.24 g (0.48 mmoles) |
| 2-Isopropoxy-1,4-naphthoquinone | 0.016 g |
| a copolymer of dimethylpolysiloxane and a polyoxyalkylene ether available under the tradename "SF-1066 Surfactant" from General Electric | 0.10 g |
| Phthalaldehyde (Control 1) or a Phthalaldehyde-adduct | 3.0 millimole (0.16 mmole/dm$^2$ of coating) |

| Formula II | |
|---|---|
| Poly(ethylene-co-1,4-cyclohexyl-enedimethylene-1-methyl-2,4-benzenedisulfonamide) binder (15% wt-wt acetone) | 10.0 g |
| Hexammine cobalt(III) trifluoroacetate | 0.24 g |
| 5,5-Diphenylhydantoin | 0.12 g |
| 3,5-Bis(trichloromethyl)-1-naphthyl-s-triazine | 0.15 g |
| "SF-1066 Surfactant" | 0.10 g |
| Phthalaldehyde (Control 2) or a Phthalaldehyde-adduct | 3.0 millimole |

TABLE III

| | | Sensitometric Results | | | |
|---|---|---|---|---|---|
| | | Negative-Working Mode | | Positive-Working Mode | |
| Example | Phthalaldehyde Source | $D_{max}/D_{min}$ | Rel. Speed Log E | $D_{max}/D_{min}$ | Rel. Speed Log E |
| Control 1 | Phthalaldehyde alone | 1.91/0.03 | 1.05 | — | — |
| Control 2 | Phthalaldehyde alone | — | — | 2.18/0.04 | 1.0 |

TABLE III-continued

| | | Sensitometric Results | | | |
|---|---|---|---|---|---|
| | | Negative-Working Mode | | Positive-Working Mode | |
| Example | Phthalaldehyde Source | $D_{max}/D_{min}$ | Rel. Speed Log E | $D_{max}/D_{min}$ | Rel. Speed Log E |
| 1 | 1-Hydroxy-3-N—imidazo-linophthalan | 2.58/— | 0 | 2.98/1.20 | 0.6 |
| 2 | 1-Hydroxy-3-bis-(methane-sulfonyl)methanophthalan | 1.25/0.02 | 1.50 | 0.04/0.02 | 0.3 |
| 3 | 1,3-Dihydroxy-N—(4-chloro-benzenesulfonyl)iso-indoline | 3.06/0.02 | 1.50 | — | — |
| 4 | 1,3-Dihydroxy-N—(4-methylbenzenesulfonyl)-isoindoline | 2.79/0.02 | 1.50 | — | — |
| 5 | 1,3-Dihydroxy-N—(4-bromo-benzenesulfonyl)iso-indoline | 3.51/0.03 | 1.35 | — | — |
| 6 | 1,3-Dihydroxy-N—(4-iodo-benzenesulfonyl)iso-indoline | 3.97/0.3 | 1.35 | — | — |
| 7 | 1,3-Dihydroxy-N—(4-acet-amidobenzenesulfonyl)-isoindoline | 3.09/0.10 | 1.35 | — | — |
| 8 | 1,3-Dihydroxy-N—(4-carbo-methoxybenzenesulfonyl)-isoindoline | 2.74/0.03 | 1.35 | — | — |
| 9 | 1,3-Dihydroxy-N—(benzene-sulfonyl)isoindoline | 3.12/0.03 | 1.50 | — | — |
| 10 | 1,3-Dihydroxy-N—(methane-sulfonyl)isoindoline | 3.45/0.05 | 1.95 | — | — |
| 11 | 1,3-Dihydroxy-N—(4-nitro-benzenesulfonyl)-isoindoline | 3.49/0.02 | 1.05 | — | — |
| 12 | 1-Hydroxy-3-trichloro-acetamidophthalan | 2.58/0.03 | 1.75 | 2.90/0.01 | 0.75 |
| 13 | 1,3-Dihydroxy-N—(dichloro-acetyl)isoindoline and 1-hydroxy-3-di-chloroacetamidophthalan | 2.70/0.03 | 1.45 | 2.90/0.01 | 0.75 |
| 14 | 1,3-Dihydroxy-N—(α-tolylsulfonyl)iso-indoline | 1.65/0.03 | 1.15 | — | — |
| 15 | 1,3-Dihydroxy-N—(4-methoxybenzenesul-fonyl)isoindoline | 2.61/0.05 | 1.28 | — | — |
| 16 | 1,3-Dihydroxy-N—(4-N,N—diethylamino)phenyl enediaminesulfonyl)-isoindoline | — | — | 1.22/0.67 | 0.90 |

The first two examples demonstrate that certain adducts provide better sensitometric results when used either in the negative-working mode or the positive-working mode, but not both. However, Examples 12 and 13 are equally effective in both.

In all of these examples, the fact that a dye image of at least 1.0 density was produced is believed to be evidence that the adduct decomposed at 135° C.

EXAMPLES 17–26

Additional Adducts Used in Imaging Elements

The procedure of Example 1 was repeated, except that the adducts were those listed in Table IV. Only $D_{max}$ values were obtained.

TABLE IV

| | | Sensitometric Results | |
|---|---|---|---|
| Example | Compound | Neg.-Working $D_{max}$ | Pos.-Working $D_{max}$ |
| 17 | 1-Hydroxy-3-(penta-fluoro-lactamidophthalan | 2.09 | — |
| 18 | 1-hydroxy-3-δ-valero-acetamidophthalan | — | 1.86 |
| 19 | 1-hydroxy-3-α-pyridone-amidophthalan | 1.96 | 1.90 |
| 20 | 1-hydroxy-3-ε-capro-lactamidophthalan | 1.20 | 2.84 |
| 21 | 1-Hydroxy-3-(3'-phthalido)phthalan | 1.17 | — |
| 22 | 1-Hydroxyphthalan-3-sulfonic acid, sodium salt | — | 1.46 |
| 23 | 1,3-Dihydroxy-N—[4-(1-hydroxyethyl)benzene-sulfonyl]isoindoline | 1.63 | — |
| 24 | 1,3-Dihydroxy-N—naphthal-enesulfonylisoindoline | 2.97 | — |
| 25 | 1,3-dihydroxy-N—[3-pyridine carbonyl]isoindoline | 1.15 | 0.06 |
| 26 | 1,3-Dihydroxy-N—[(2,5-dichloro)benzenesul-fonyl]isoindoline | 1.01 | — |

EXAMPLES 27–31

Use of Adducts to Provide Imagewise Plasticizing

The procedure of Example 1 was followed, except that the adducts were the adducts of Table V. Some of these were prepared in situ as noted. After the coatings were prepared, they were exposed on an Ascor Vacuum Printer for 20–40 sec and processed for 5 sec at 125° C. in a thermal processor similar to that described in Research Disclosure 17623, Vol. 176, published 12/78, p. 9. The Tg (glass transition) temperature was measured respectively in a $D_{min}$ or $D_{max}$ area and the percent processing dimensional change (PDC) as a result of thermal processing was also measured. Table V summarizes the results. For each of the adduct coatings, whether the adduct was formed ex situ of in situ, the difference between $D_{max}$ percent processing dimensional change and $D_{min}$ percent processing dimensional change is minimized.

TABLE VI

| Ex. | Adduct | Mode | $D_{max}$ |
|---|---|---|---|
| 37 | 1-Hydroxy-3-(4-chlorobenzamido)-phthalan, described in J. Org. Chem., Vol. 35, p. 3940 | Negative working | 0.92 |
| 38 | 1-Hydroxy-3-(2-fluorobenzamido)-phthalan | Negative working | 0.92 |
| 39 | 1,3-Dihydroxy-N-(hexadecylsulfonyl)isoindoline | Negative working | 0.82 |

The invention has been described in detail with particular reference to preferred embodiments thereof, but it will be understood that variations and modifications can be effected within the spirit and scope of the invention.

What is claimed is:

TABLE V

| Example | Phthalaldehyde Source | Mode | Tg, °C. $D_{max}$ | $D_{max}$ | $D_{min}$ | ΔTg, °C. | % PDC $D_{max}$ | $D_{min}$ | Δ % PDC |
|---|---|---|---|---|---|---|---|---|---|
| Control 3 | Phthalaldehyde alone | negative working | 3.72 | 80 | 40 | 40 | −0.070 | −0.039 | 0.031 |
| 27 | 1,3-Dihydroxy-N-(4-chlorobenzenesulfonyl)isoindoline | negative working | 3.72 | 48 | 32 | 16 | −0.029 | −0.032 | 0.003 |
| 28 | 1,3-Dihydroxy-N-(4-methylbenzenesulfonyl)isoindoline | negative working | 3.70 | 48 | 27 | 21 | −0.031 | −0.038 | 0.007 |
| 29 | 1,3-Dihydroxy-N-(4-chlorobenzenesulfonyl)isoindoline* | negative working | 3.55 | 50 | 32 | 18 | −0.023 | −0.033 | 0.010 |
| 30 | 1,3-Dihydroxy-N-(4-methylbenzenesulfonyl)isoindoline* | negative working | 3.38 | 45 | 31 | 14 | −0.030 | −0.032 | 0.002 |
| Control 4 | Phthalaldehyde alone | Positive working | 3.32 | 77 | 37 | 40 | −0.073 | −0.044 | 0.029 |
| 31 | 1-Hydroxy-3-trichloroacetamido)-phthalan | Positive working | 3.54 | 50 | 26 | 24 | −0.048 | −0.052 | 0.004 |

*Prepared in situ by adding the constituent materials of the adduct to the dope.

EXAMPLES 32–36

To demonstrate the "simplified test" described above wherein adduct solutions were imbibed into filter paper, procedure of that test was followed, viz:

Solutions were prepared using the Part A and Part B mixes described above. For each adduct, Parts A and B are admixed and imbibed into the filter paper. The treated papers were dried in a hood for 30 minutes, exposed as noted above for the "simplified test", and heated for 10 sec on a 135° C. hot block. Dyes were found to form for adducts of Examples 3, 4, 12 and 13, as well as for 1,3-dihydroxy-N-(n-butyramido)isoindoline, an adduct described in J. Org. Chem., Vol. 35, p. 3940–3943 (1975).

EXAMPLES 37–39

The procedure of Example 1 was repeated, except that the adducts of Table VI were used. As is apparent from the $D_{max}$ values of Table VI, although these adducts formed dyes, the dyes did not have the preferred density of 1.0 or greater.

1. In an unexposed imaging composition comprising a source of phthalaldehyde and an energy-activatible material capable of generating an amine that reacts with said phthaladehyde to form a dye, said material including a cobalt(III) complex;
    the improvement wherein said source of phthalaldehyde comprises an adduct of phthalaldehyde in an amount sufficient to produce in said composition a maximum neutral density of at least 1.0, when coated onto a support in an amount of about 0.16 mmoles/dm², dried and exposed at a distance of 2.5 cm for 30 sec to three 60-watt UV-fluorescent lamps and developed by heating for 10 sec at a temperature of 135° C.

2. A composition as defined in claim 1, wherein said adduct contains a heat-releasable sulfonamide or carbonamide.

3. A composition as defined in claim 1, wherein said adduct is an isoindoline.

4. A composition as defined in claim 1, wherein said adduct is a phthalan.

5. A composition as defined in claim 1, wherein said energy-activatable material comprises a reducible complex containing releasable ligands at least one of which is said amine, and a destabilizer material capable of causing release of said ligands upon exposure to activating energy.

6. A composition as defined in claim 5, wherein said destabilizer material is a photoreductant.

7. A composition as defined in claim 5, wherein said destabilizer material is thermally activatible.

8. A composition as defined in claim 1, wherein said adduct of phthalaldehyde produces a plasticizer for said composition when heated to a temperature of 125° C.

9. A composition as defined in claim 8, wherein said adduct is an isoindoline.

10. A composition as defined in claim 8, wherein said adduct is a phthalan.

11. A radiation-sensitive imaging element comprising a support having thereon a composition as defined in any one of claims 2-8, 10 and 12.

12. In an unexposed imaging composition comprising a source of phthalaldehyde and an energy-activatible material capable of generating an amine that reacts with said phthalaldehyde to form a dye, said material including a cobalt(III) complex; the improvement wherein said source of phthaldehyde comprises an adduct of phthalaldehyde, in an amount sufficient to produce a dye having a maximum neutral density of at least 1.0 when said composition comprises an amount of about 3.0 mmoles of said adduct and about 0.50 mmoles of a source of amines, and said composition is coated onto a support at a rate of about 0.16 mmoles/dm$^2$ of said adduct, dried, exposed at a distance of 2.5 cm for 30 sec to three 60-watt UV-fluorescent lamps, and heated for 10 sec at a temperature of 135° C.

13. A composition as defined in claim 12, wherein said composition is present in at least one layer of an imaging element, and wherein said adduct includes a plasticizer for said composition.

* * * * *